United States Patent
Donlon et al.

(10) Patent No.: US 11,224,733 B2
(45) Date of Patent: Jan. 18, 2022

(54) COMPLEX IRRIGATION/SUCTION FLOW PATH IN A MEDICAL DEVICE

(71) Applicant: INTUITIVE SURGICAL OPERATIONS, INC., Sunnyvale, CA (US)

(72) Inventors: Edward P. Donlon, San Jose, CA (US); Craig Tsuji, San Jose, CA (US)

(73) Assignee: INTUITIVE SURGICAL OPERATIONS, INC., Sunnyvale, CA (US)

(*) Notice: Subject to any disclaimer, the term of this patent is extended or adjusted under 35 U.S.C. 154(b) by 800 days.

(21) Appl. No.: 15/897,832

(22) Filed: Feb. 15, 2018

(65) Prior Publication Data

US 2018/0229021 A1   Aug. 16, 2018

Related U.S. Application Data

(60) Provisional application No. 62/459,708, filed on Feb. 16, 2017.

(51) Int. Cl.
*A61M 39/22* (2006.01)
*A61B 34/35* (2016.01)
(Continued)

(52) U.S. Cl.
CPC .......... *A61M 39/223* (2013.01); *A61B 34/35* (2016.02); *A61M 1/774* (2021.05); *A61M 3/022* (2014.02);
(Continued)

(58) Field of Classification Search
CPC ............ A61M 39/223; A61M 39/0208; A61M 1/774; A61M 3/022; A61M 3/0212; A61M 3/0283; A61M 39/225; A61M 2039/226; A61M 2039/2473; A61M 2039/2486; A61M 1/0058; A61M 1/0062; F16K 3/26;
(Continued)

(56) References Cited

U.S. PATENT DOCUMENTS 5,490,836 A * 2/1996 Desai ............... A61B 17/00234
                                                          604/21
5,722,949 A * 3/1998 Sanese ................ A61M 1/0064
                                                          604/119

(Continued)

OTHER PUBLICATIONS

Co-pending U.S. Appl. No. 29/581,071, filed Oct. 14, 2016.

(Continued)

*Primary Examiner* — Theodore J Stigell
(74) *Attorney, Agent, or Firm* — Haynes and Boone, LLP (57) ABSTRACT

A suction/irrigation medical device valve system comprises a first valve plunger configured for insertion into a first valve plunger channel. The first valve plunger has a first latch member disposed at a distal end with a first sealing member and a first valve opening disposed proximally from the first latch member. The system also comprises a second valve plunger configured for insertion into a second valve plunger channel. The second valve plunger includes a second valve opening that is longer than the first valve opening. The system also comprises a valve body having the first and second valve plunger channels. The first and second valve plunger channels are configured to receive the first and second valve plungers, respectively.

10 Claims, 11 Drawing Sheets

(51) Int. Cl.
  *A61M 3/02* (2006.01)
  *F16K 3/26* (2006.01)
  *F16K 11/16* (2006.01)
  *F16K 27/06* (2006.01)
  *F16K 31/53* (2006.01)
  *A61M 1/00* (2006.01)
  *F16K 11/10* (2006.01)
  *A61B 34/30* (2016.01)
  *A61M 39/24* (2006.01)

(52) U.S. Cl.
  CPC ........ *A61M 3/0208* (2014.02); *A61M 3/0212* (2014.02); *A61M 3/0283* (2013.01); *A61M 39/225* (2013.01); *F16K 3/26* (2013.01); *F16K 11/165* (2013.01); *F16K 27/065* (2013.01); *F16K 31/535* (2013.01); *A61B 2034/305* (2016.02); *A61M 2039/226* (2013.01); *A61M 2039/2473* (2013.01); *A61M 2039/2486* (2013.01); *A61M 2205/584* (2013.01); *F16K 11/10* (2013.01)

(58) Field of Classification Search
  CPC .... F16K 11/165; F16K 27/065; F16K 31/535; F16K 11/10; A61B 34/35; A61B 2034/305
  See application file for complete search history.

(56) References Cited

U.S. PATENT DOCUMENTS

| | | | | |
|---|---|---|---|---|
| 6,375,653 | B1* | 4/2002 | Desai | A61B 17/00234 604/131 |
| 6,419,654 | B1* | 7/2002 | Kadan | A61B 1/00068 600/101 |
| 6,652,488 | B1* | 11/2003 | Cover | A61M 1/774 604/118 |
| 6,808,505 | B2* | 10/2004 | Kadan | A61B 1/00068 604/164.04 |
| 6,958,058 | B1* | 10/2005 | Hunter, Sr. | A61M 1/0058 604/500 |
| 8,241,271 | B2 | 8/2012 | Millman et al. | |
| 9,259,519 | B2* | 2/2016 | Fedenia | A61B 18/12 |
| 10,155,072 | B2* | 12/2018 | Teng | A61M 39/22 |
| 10,722,620 | B2* | 7/2020 | Chuang | A61M 3/0283 |
| 2003/0120203 | A1* | 6/2003 | Guo | A61M 1/0064 604/35 |
| 2007/0005002 | A1 | 1/2007 | Millman et al. | |
| 2007/0156121 | A1 | 7/2007 | Millman et al. | |
| 2009/0099520 | A1 | 4/2009 | Millman et al. | |
| 2011/0230823 | A1* | 9/2011 | Simonsen | A61M 1/0064 604/30 |
| 2013/0046318 | A1 | 2/2013 | Radgowski et al. | |
| 2019/0038816 | A1* | 2/2019 | Nobis | A61M 3/022 |

OTHER PUBLICATIONS

Co-pending U.S. Appl. No. 29/581,072, filed Oct. 14, 2016.
Co-pending U.S. Appl. No. 29/581,073, filed Oct. 14, 2016.
Co-pending U.S. Appl. No. 29/581,074, filed Oct. 14, 2016.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

COMPLEX IRRIGATION/SUCTION FLOW PATH IN A MEDICAL DEVICE

PRIORITY INFORMATION

This application is a non-provisional application claiming priority to U.S. Provisional Application No. 62/459,708, filed Feb. 16, 2017, the disclosure of which is incorporated herein by reference in its entirety.

FIELD

The present disclosure relates generally to medical instruments, and more particularly to the flow path of steerable and articulate medical instruments having robotically actuated features and manually actuated features.

BACKGROUND

In the field of robotic surgery and machine-aided medical procedures there is the need to rapidly and efficiently introduce material to, and remove material from, the interventional area. For example, in some situations it is desirable to remove blood or other liquid or solid material accumulation near the interventional site in order to maintain good visibility for the physicians. Similarly, it is desirable to remove smoke during endoscopic procedures to maintain good visibility. In some situations it is desirable to introduce a gas to inflate a body cavity that includes an organ or a tissue that is involved in surgery. Such insufflation provides sufficient space for the physician to manually or robotically manipulate instruments and for an adequate endoscopic field of view. In other situations, it may be desirable to irrigate the interventional area (e.g., with water or a saline solution), either for allowing visibility of the area of interest or to provide moisture to the tissue surrounding the area of interest.

However, some conventional irrigation/suction instruments can become clogged as material moves through the flow path. This decreases the performance of such instruments and can lead to decreased visibility and slower removal of material from the interventional site. What is needed is a medical instrument that provides the improved performance during suction and irrigation operation.

SUMMARY

The embodiments of the invention are best summarized by the claims that follow the description.

Consistent with some embodiments, a suction/irrigation medical device is provided. An exemplary suction/irrigation medical device includes a valve body having one or more conduits fluidically coupled thereto, a first channel extending through the valve body, and first and second valve plungers. The first valve plunger is disposed along the first channel and is configured to move along an axis to open and close the first channel. The first valve plunger has a first opening to permit a fluid to flow through the first channel. The second valve plunger is disposed along the first channel and along a second channel to couple the second channel into the first channel when the second valve plunger is in a first position. The second valve plunger has a second opening that has at least one dimension that is greater than a corresponding dimension of the first opening of the first valve plunger.

Consistent with some embodiments, a valve system is provided. An exemplary valve system includes first and second valve plungers. The first valve plunger is configured for insertion into a first valve plunger channel and has a first latch member disposed at a distal end, a first sealing member, and a first valve opening disposed proximally from the first latch member. The second valve plunger is configured for insertion into a second valve plunger channel and has a second valve opening that is longer than the first valve opening. The exemplary valve system further includes a valve body having the first and second valve plunger channels, the first and second valve plunger channels being configured to receive the first and second valve plungers, respectively.

Consistent with some embodiments, a medical system is provided. An exemplary medical system includes a backend housing that receives a first conduit and a second conduit. The first conduit configured for communication with a pressurized fluid source and the second conduit configured for communication with a vacuum source. The backend house further contains a valve body coupled to the first and second conduits, the valve body including a first valve plunger channel and a second valve plunger channel. The backend housing further contains first and second valve plungers. The first valve plunger being is into the first valve plunger channel and includes a first valve opening. The second valve plunger being inserted into the second valve plunger channel, the second valve plunger including a second valve opening that is longer than the first valve opening, with the first valve plunger channel being configured in parallel with the second valve plunger channel. The backend housing further includes a first manual actuation button coupled to the first valve plunger and a second manual actuation button coupled to the second valve plunger. The exemplary medical system further includes an elongate instrument shaft protruding distally from a chassis portion the backend housing. The chassis portion is configured to couple to a robotic control interface to permit remote control of the first valve plunger and the second valve plunger.

Consistent with some embodiments, another medical device is provided. An exemplary medical device includes a valve body, in which a first fluid channel and a second fluid channel are defined, wherein the first fluid channel extends through the valve body and comprises a proximal portion, a middle portion, and a distal portion, and wherein the second fluid channel extends into the valve body. The exemplary medical device further includes a first valve plunger and a second valve plunger. The first valve plunger includes a first fluid path is defined therethrough. The first plunger is movable between a first position, in which the first valve plunger is positioned to obstruct fluid flow between the proximal and middle portions of the first channel, and a second position, in which the first fluid path couples the proximal and middle portions of the first fluid channel. The second valve plunger includes a second fluid path is defined therein. The second plunger is movable between a first position, in which the second fluid path is positioned to couple the middle and distal portions of the first fluid channel and to obstruct fluid flow between the second channel and the distal portion of the first channel, and a second position, in which the second fluid path couples the second fluid channel to the distal portion of the first fluid channel.

Consistent with some embodiments, another medical device is provided. An exemplary medical device includes a first fluid channel defined in the medical device and a second fluid channel defined in the medical device. The exemplary medical device further includes a first valve plunger comprising a button comprising a convex top surface and a second valve plunger comprising a button comprising a concave top surface. The first valve plunger is positioned to control a fluid flow in the first fluid channel. The second valve plunger is positioned to control a fluid flow in the second fluid channel. The button of the first valve plunger and the button of the second valve plunger are positioned adjacent one another.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

Embodiments of the present disclosure and their advantages are best understood by referring to the detailed description that follows. It should be appreciated that like reference numerals are used to identify like elements illustrated in one or more of the figures, wherein showings therein are for purposes of illustrating embodiments of the present disclosure and not for purposes of limiting the same.

DETAILED DESCRIPTION

In the following description, specific details are set forth describing some embodiments consistent with the present disclosure. Numerous specific details are set forth in order to provide a thorough understanding of the embodiments. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional. In some instances well known methods, procedures, components, and circuits have not been described in detail so as not to unnecessarily obscure aspects of the embodiments.

The present application is related to the following U.S. patent applications, all assigned to Intuitive Surgical Operations, Inc. or to Intuitive Surgical, Inc., the contents of which are incorporated herein by reference in their entirety and for all purposes: U.S. patent application Ser. No. 11/341,004 (filed Jan. 27, 2006; entitled "Robotic Surgical Instruments for Irrigation, Aspiration, and Blowing" by Millman et al.); U.S. patent application Ser. No. 11/341,155 (filed Jan. 27, 2006; entitled "Robotic Surgical Instruments with a Fluid Flow Control System for Irrigation, Aspiration, and Blowing" by Millman et al.); U.S. patent application Ser. No. 11/454,359 (filed Jun. 15, 2006; entitled "Robotic Surgical Systems with Fluid Flow Control for Irrigation, Aspiration, and Blowing" by Millman et al.); U.S. patent application Ser. No. 11/454,476 (filed Jun. 15, 2006; entitled "Methods of Fluid Flow Control with Robotic Surgical Instruments for Irrigation, Aspiration, and Blowing" by Millman et al.); and U.S. patent application Ser. No. 13/446,978 (filed Apr. 13, 2012; entitled "Surgical Instrument with Commonly Actuated Robotic and Manual Features" by Radgowski et al.).

Figure 1:
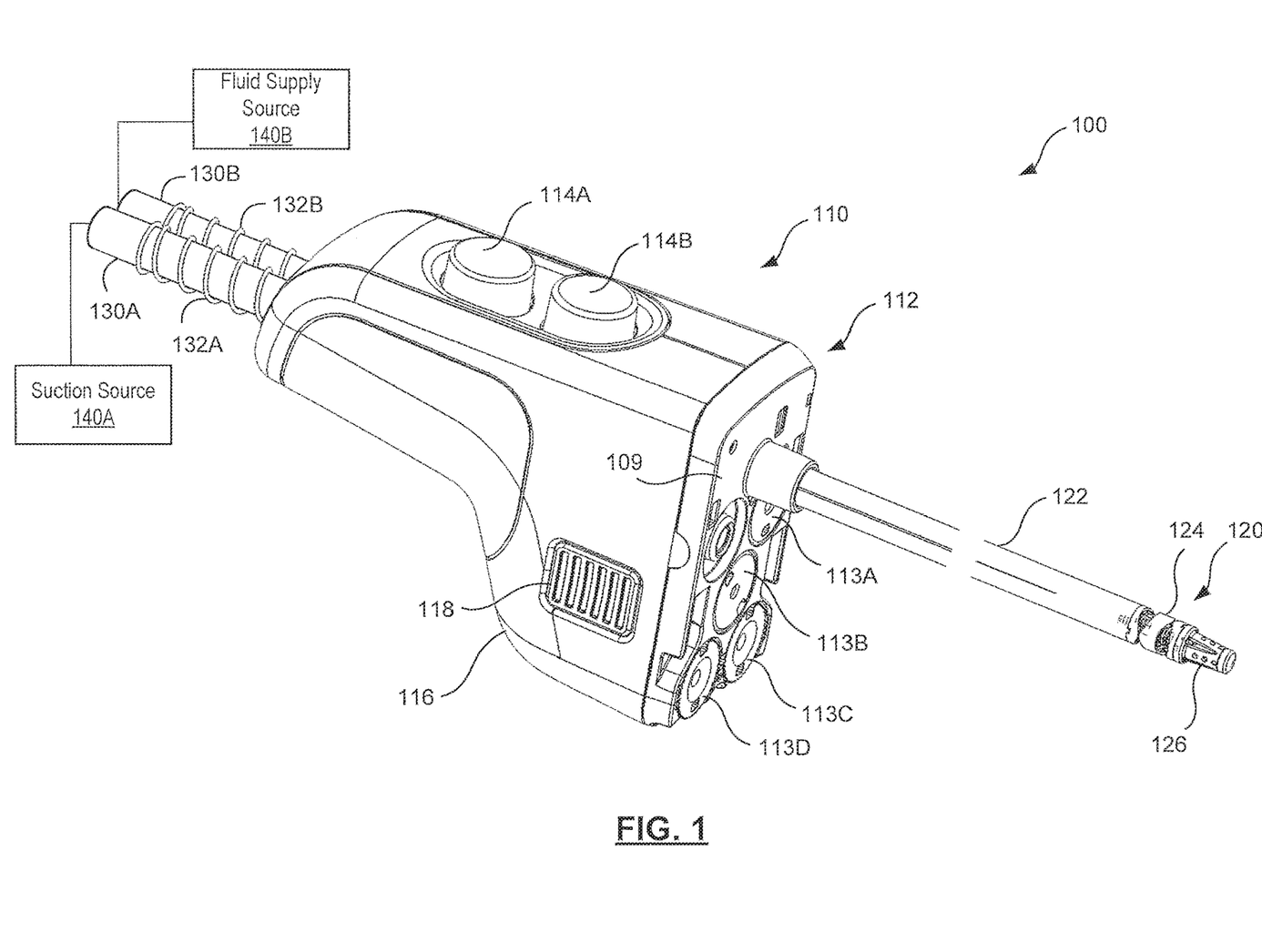
FIG. 1 is a perspective view of a medical instrument system according to some embodiments.

FIG. 1 is a perspective view of a medical instrument system 100 according to some embodiments of the present disclosure. The medical instrument system 100 includes a backend mechanism 110 and an elongate instrument portion 120 that is coupled to the backend mechanism 110 at a proximal end of a shaft 122 that forms part of the elongate instrument portion 120. The instrument portion 120 further includes a wrist mechanism 124 and an end effector 126. The wrist mechanism 124 is coupled to a distal end of the shaft 122.

The backend mechanism 110 may include a chassis 112 that has an interface faceplate 109 configured to interface with a teleoperational medical system, according to some embodiments. For example, the chassis 112 may couple to or include gears and interface discs, like exemplary interface discs 113A and 113B, configured to connect to an instrument interface on a medical robotic system, such as a da Vinci® model surgical system instrument manipulator arm commercialized by Intuitive Surgical, Inc. of Sunnyvale, Calif. Some embodiments of the mechanism 110 may omit the chassis 112. Embodiments of the instrument system 100 that include the chassis 112 may provide for both manual and robotically-controlled actuation of the medical instrument system 100. The backend mechanism 110 further includes a first button 114A and a second button 114B, collectively referred to as buttons 114. As described in more detail herein, the buttons 114 may control suction, ventilation, and/or irrigation functions provided by the medical system 100. The contact surface of the buttons 114, i.e. the surface that would generally be in the most contact with the finger of an operator, may be straight, convex, or concave. In some embodiments, the contact surface of the button 114A is convex, while the contact surface of the button 114B is concave. In some other embodiments, the contact surface of the button 114A may be concave, while the contact surface of button 114B is convex. Additionally, the buttons 114 may have the same color or different colors. For example, whichever button has a convex contact surface may be grey, while the button having the concave surface may be blue. Additional details may be found in U.S. Design patent application Nos. 29/581,074, 29/581,071, 29/581,072, and 29/581,073, all of which were filed on Oct. 14, 2016 and are incorporated by reference herein in their entirety.

The backend mechanism 110 includes a rigid housing 116 and includes at least one release mechanism 118. An operator of the medical system 100 may couple and decouple the medical system 100 to a robotic arm or other robotic manipulator by pressing the release mechanism 118. Some embodiments may include a release mechanism 118 on the side of the medical system 100 and another release mechanism on the opposite side thereof.

The backend mechanism 110 may be coupled to a console (not explicitly depicted) by conduit such as the first tubing 130A and second tubing 130B. An exemplary console may include a suction source 140A and a liquid or other fluid supply source 140B. The suction source 140A provides a fluid suction flow to remove material from an interventional site. The fluid supply source 140B provides a fluid supply flow, which may be a flow of saline, an inert gas, or another fluid. The tubing 130A and 130B, collectively referred to as tubing 130, may be supported by springs 132A and 132B which extend over a distal portion of the tubing 130A and 130B, respectively. The springs 132 may provide resistance to prevent collapsing or kinking of the tubing 130 near the junction with the backend mechanism 110.

Figure 2:
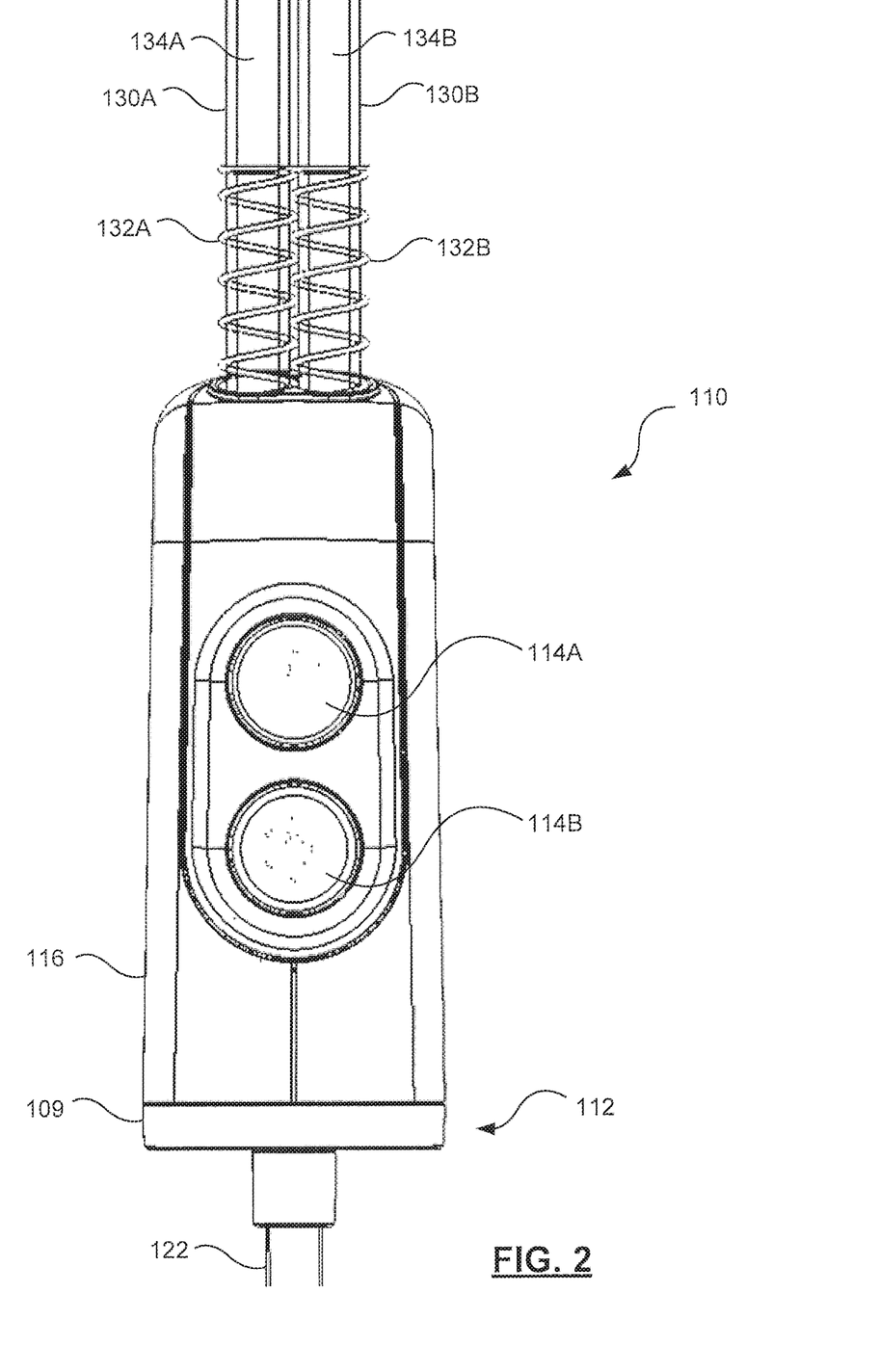
FIG. 2 is a front elevation view of the medical instrument system of FIG. 1 according to some embodiments.

FIG. 2 is a front elevation view of the medical instrument system 100 of FIG. 1, according to some embodiments. In the view provided by FIG. 2, the tubing 130 is depicted as transparent, such that interior lumens 134A and 134B are shown. A proximal end of the lumen 134A (not shown) may be coupled to a pressurized liquid system that provides a liquid for use at an interventional site. A proximal end of the lumen 134B (not shown) may be coupled to a system of pressurized air disposed in a console. In some embodiments, the pressurized air system may include a vacuum to facilitate suction or aspiration of material through the lumen 134B. The pressurized air system may additionally include a pump to facilitate ventilation through the lumen 134B. As is described in more detail herein, the backend mechanism includes a valve system that couples the lumens 134A and 134B to a lumen extending within the shaft 122 to the distal end thereof.

Figure 3:
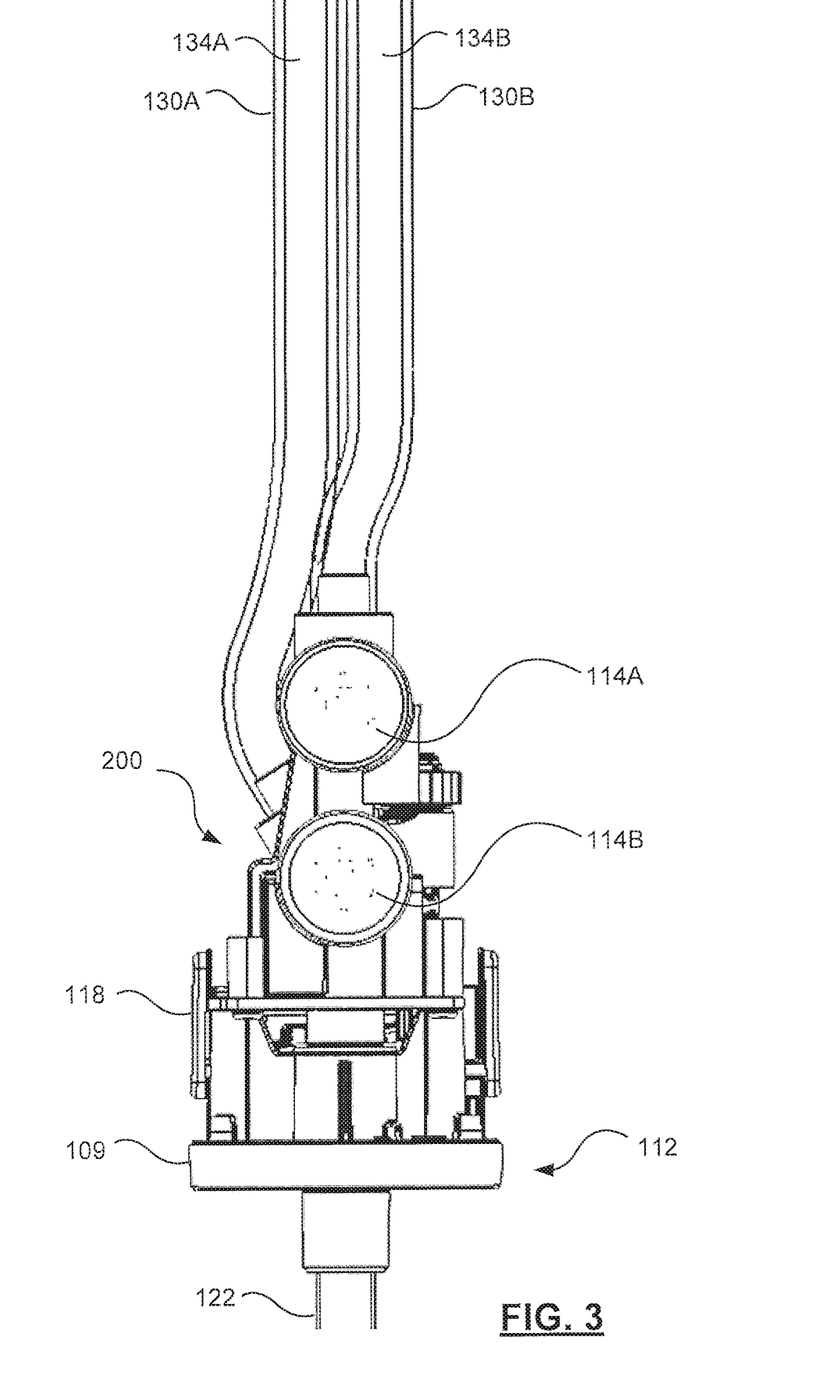
FIG. 3 is another front elevation view of the medical instrument system of FIG. 1 with an instrument housing removed to show details according to some embodiments.

FIG. 3 is another front elevation view of the medical instrument system of FIG. 1 with an instrument housing removed to show details according to some embodiments. FIG. 3 depicts a valve system 200 that, either by robotic control or manual control, selectively couples at least one of the lumens 134A and 134B to the shaft 122 of the elongate instrument portion 120.

Figure 4:
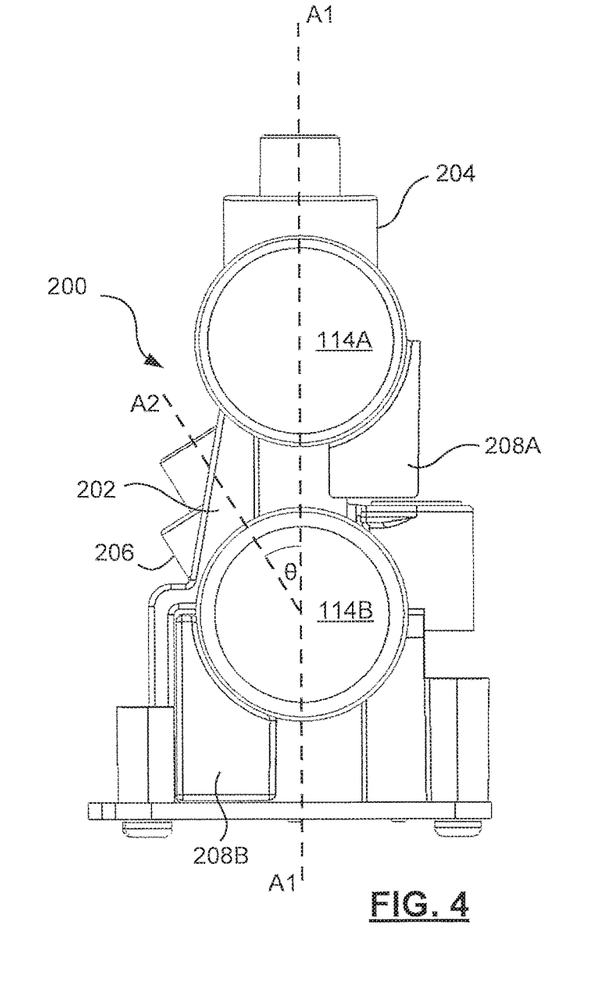
FIG. 4 is a front elevation view of a valve system shown in FIG. 3 according to some embodiments.

FIG. 4 is a front elevation view of the valve system 200 shown in FIG. 3 according to some embodiments. As shown in FIG. 4, and in other figures, the valve system 200 includes a valve body 202 having flow paths defined therein as well as openings and channels for valve plungers and other features as described herein. The valve body 202 may be formed from a rigid material, such as a rigid plastic material or metal. The buttons 114 are disposed along an axis A1. A first tubing coupler 204 is disposed along the axis A1. A second tubing coupler 206 is formed in the valve body 202 and oriented along an axis A2 that forms an angle with the axis A1. This angle, referred to as angle θ1, may range from about 10 degrees to about 45 degrees. FIG. 4 also depicts actuation members 208A and 208B, collectively actuation members 208, which are coupled to the buttons 114A and 114B, respectively. The actuation members 208A and 208B may be formed integrally with the buttons 114A and 114B in some embodiments. The actuation members 208 may couple the buttons 114 to gears or other drive mechanisms disposed on the chassis 112 of FIG. 1 to permit the buttons 114 to be manipulated by an operator via a robotic medical system.

Figure 5A:
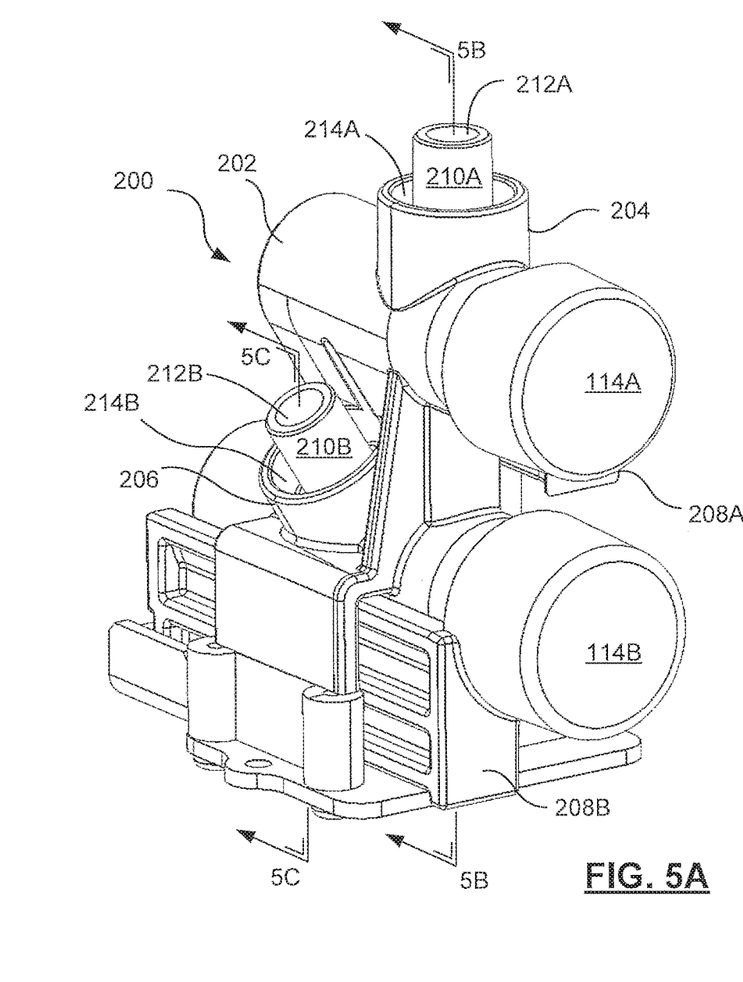
FIG. 5A is a perspective view of the valve system of FIG. 4 according to some embodiments.

FIG. 5A is a perspective view of the valve system of FIG. 4 according to some embodiments. Each of the tubing couplers 204 and 206 may include a stem 210 having a channel 212 formed therein. The stem 210 has a smaller outer diameter than a surrounding portion of the valve body 202 such that the stem 210 and the surrounding portion of the valve body 202 form a recess 214 that is configured to receive the tubing, such as the tubing 130B as shown in FIG. 3. As shown, the tubing coupler 204 includes a stem 210A having a channel 212A. The stem 210A is surrounded by a recess 214A. The tubing coupler 206 includes a stem 210B having a channel 212B to be formed therein. The stem 210B is surrounded by a recess 214B into which the tubing 130A may be inserted.

Figure 5B:
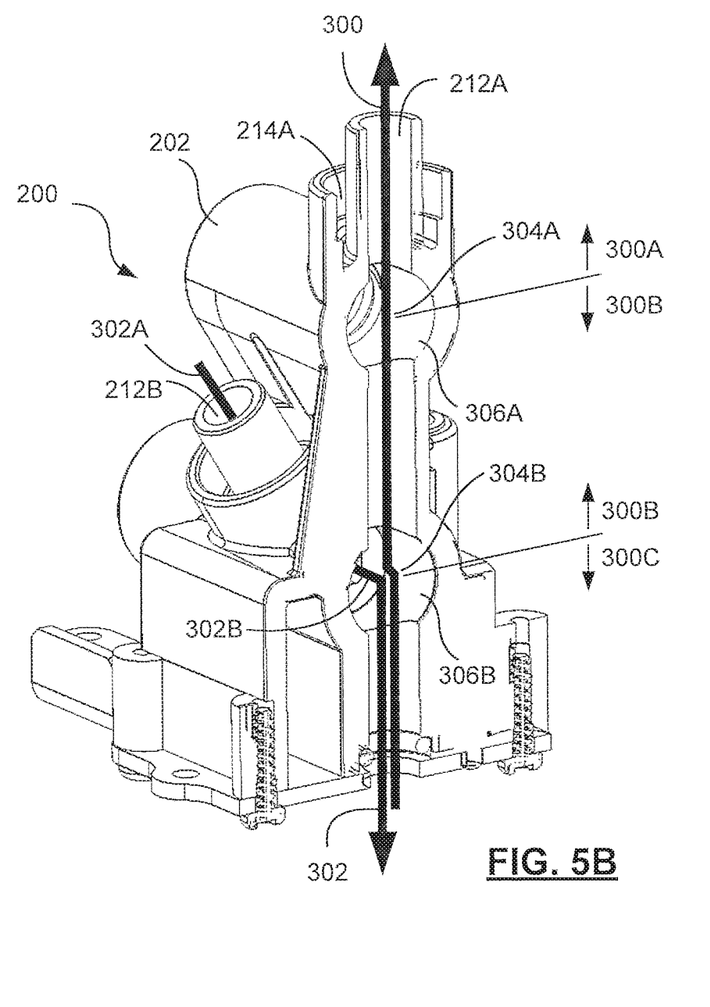
FIGS. 5B and 5C are perspective cross-sectional views of the valve system shown in FIG. 5A according to some embodiments.
Figure 5C:
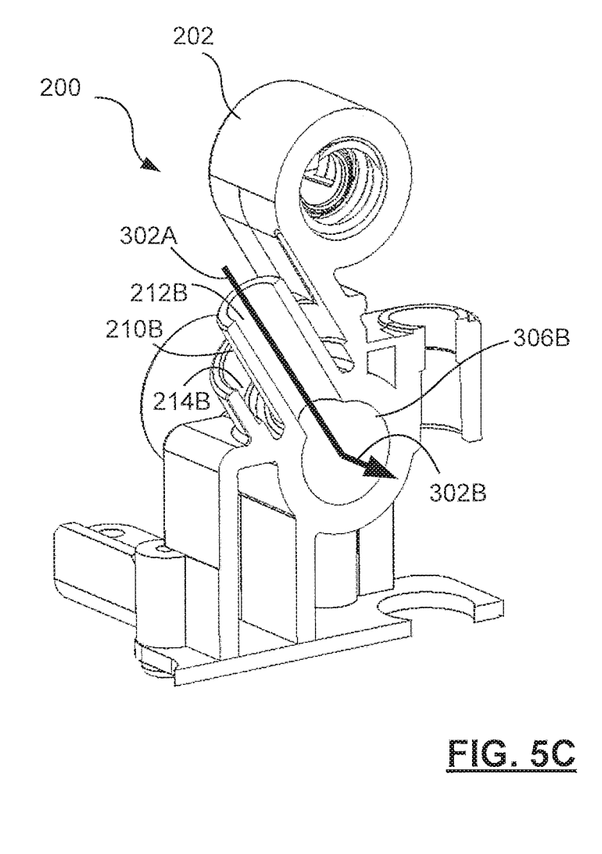

FIGS. 5B and 5C are perspective cross-sectional views of the valve system shown in FIG. 5A according to some embodiments, according to the cross-sectional indicators 5B and 5C as shown in FIG. 5A. FIG. 5B shows a complete suction flow path 300 extending through the channel 212A in the valve body 202. The flow path 300 may extend in a straight line through the valve body 202 as shown in FIG. 5B. As illustrated, the arrow representing the flow path 300 includes a slight jog to facilitate the simultaneous depiction of the flow path 300 and a flow path 302, another fluid path through which irrigation fluid may flow to the lumen of the shaft 122 as shown in FIG. 1. The flow path 300 may be a straight flow path through the valve body 202. The flow path 300 may be referred to by component portions 300A, 300B, and 300C. The flow path 300 may include a proximal portion 300A located proximally from a junction 304A of the fluid channel 212A and a valve plunger channel 306A intersect. The flow path 300 further includes a middle portion 300B that extends distally from the junction 304A to a junction 304B along the flow path 300. The junction 304B occurs at the intersection of the fluid channel 212A and a valve plunger channel 306B. The additional valve plunger channel 306A intersects the channel 212A at a distal position. The portion of the flow path 300 disposed distally from the junction 304B may be referred to as the distal portion 300C of the flow path 300.

The flow path 302 includes a proximal portion 302A extending through the channel 212B along the axis A2 of FIG. 4. The proximal portion 302A forms a junction with the valve plunger channel 306B at a bend of the flow path 302. As illustrated in FIGS. 5B and FIG. 6B the bend may have an angle of about 90 degrees. However, the angle of the bend may be different in other embodiments. An intermediate portion 302B of the flow path 302 extends along the valve plunger channel 306B to the junction 304B. Thereafter, the distal portion of the flow path 302 is in common with the distal portion 300C of the flow path 300. FIG. 5C shows a perspective cross-section according to the cross-sectional indicator 5C as shown in FIG. 5A. FIG. 5C shows a cross-section parallel to the central axis of the channel 212B.

Figure 6A:
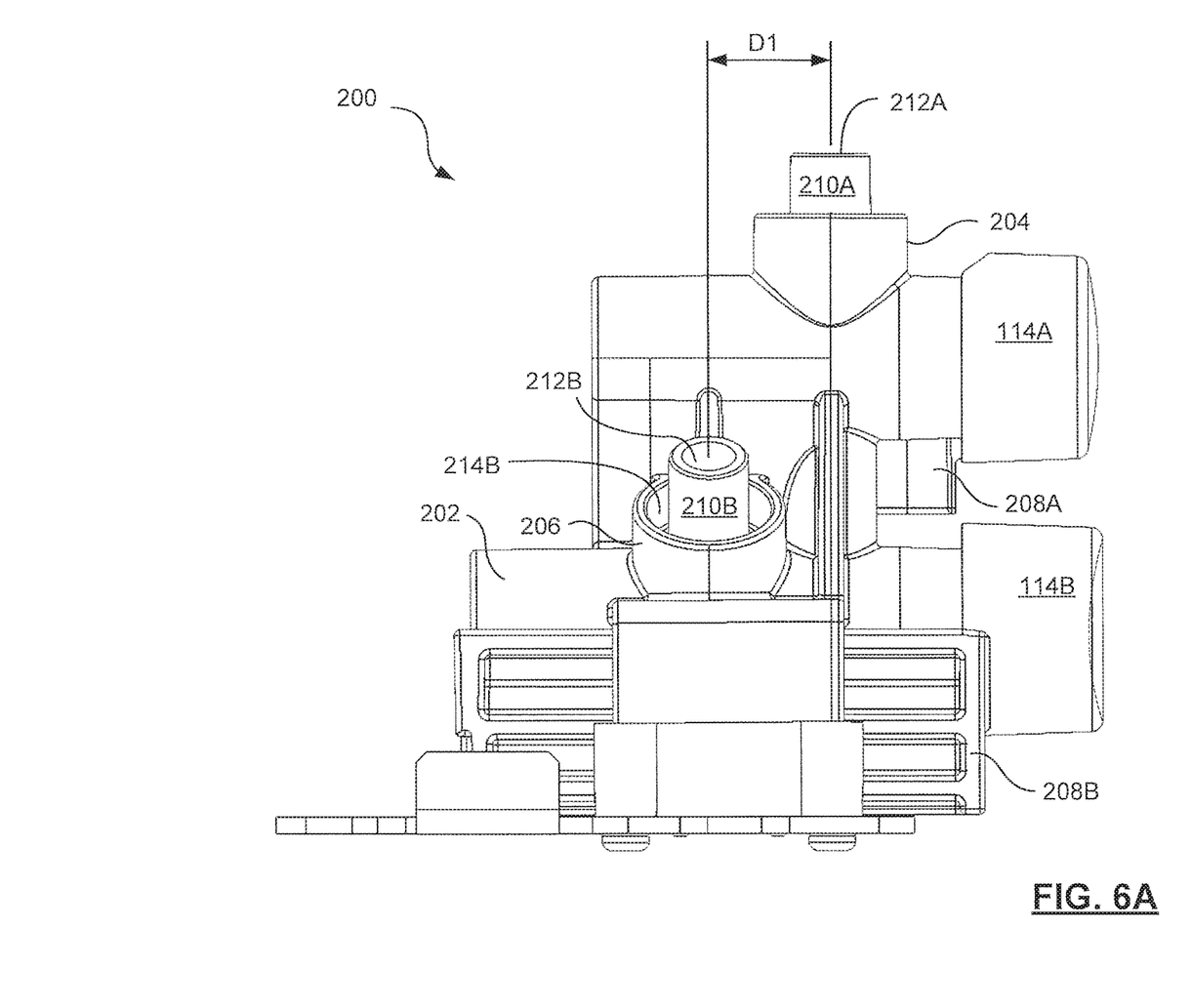
FIG. 6A is a side view of the valve system according to some embodiments.
Figure 6B:
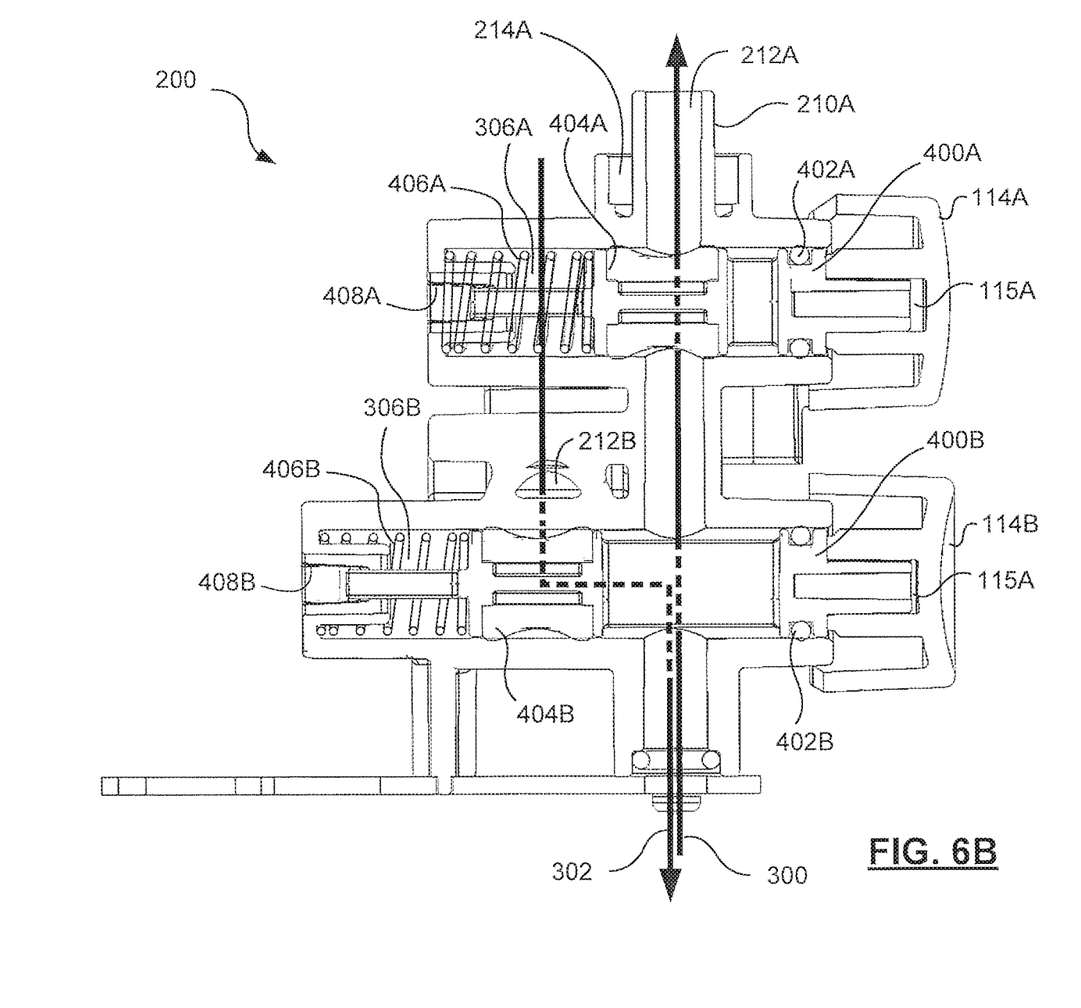
FIG. 6B is a cross-sectional side view of the valve system of FIG. 6A according to some embodiments.

FIG. 6A is a side view of the valve system 200 according to some embodiments. The centers of the channels 212A and 212B are separated by distance D1. As illustrated, the distance D1 is about 10 mm. In embodiments of the valve system 200 the distance D1 a range from about 5 mm to about 30 mm or more. FIG. 6B is a cross-sectional side view of the valve system 200 of FIG. 6A according to some embodiments. The cross-section is obtained along the axis A1 shown in FIG. 4, through both of the buttons 114. As shown in cross-section, each of the buttons 114 includes a central recess 115, labeled as central recess 115A and 115B, respectively. The central recess is 115A and 115B are respectively coupled to valve plungers 400A and 400B. The plungers 400A and 400B are disposed within the valve plunger channels 306A and 306B, respectively.

The plungers 400A and 400B each include at least one O-ring and sealing member. As shown in FIG. 6B, the O-ring 402A is positioned closer to the sealing member 404A (both of the valve plunger 400A) then the O-ring 402B and the sealing member 404B (both of the valve plunger 400B). Disposed within the valve plunger channels 306A and 306B are disposed bias elements 406A and 406B, respectively. As shown, the bias elements 406 are coil springs formed from a resilient polymer or metal. A distal end of each of the bias elements 406A and 406B contacts a surface of the respective valve plunger 400A and 400B. A proximal end of each of the bias elements 406 contacts a proximal end of the valve plunger channels 306A and 306B, respectively, to bias the plungers 400 in an extended position. By physically placing sufficient pressure on the buttons 114A and/or 114B, an operator may manually activate the valve system 200, shifting the plungers 400 within their respective channels. Proximal most portions of the plungers 400 are disposed within recesses 408A and 408B that have walls configured to maintain alignment of the plungers 400 within the channels 306A and 306B, respectively.

Figures 7A, 7B:
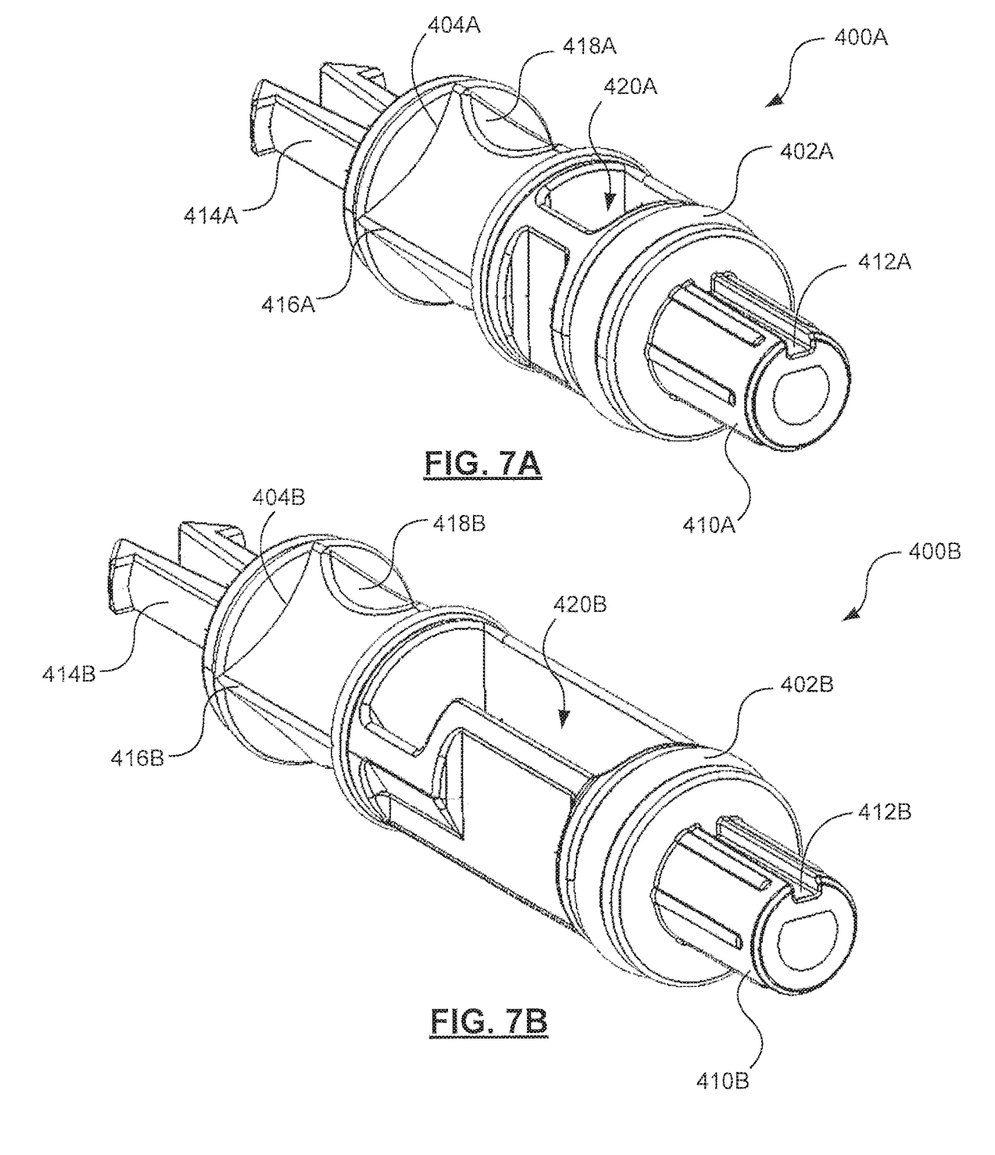
FIGS. 7A and 7B are perspective views of valve plungers according to some embodiments.

FIGS. 7A and 7B are perspective views of valve plungers 400A and 400B according to some embodiments. As seen in FIG. 7A, the valve plunger 400A includes the O-ring 402A and the sealing member 404A. At a distal end, the valve plunger includes a protrusion 410A that is sized for insertion into the recess 115A of the button 114A. To ensure alignment of the button 114A, the protrusion 410A includes a notch 412A that interfaces with a corresponding boss disposed on the surface of the recess 115A. The proximal end of the valve plunger 400A includes a latch member 414A. The latch member is configured with two compressible prongs that flex when the valve plunger 400A is inserted into the channel 306A. Each of the prongs includes a hook shape that conforms to the dimensions of the recess 408A shown in FIG. 6B and the service to prevent the valve plunger 400A from being removed from the channel 306A. The sealing member 404A is formed from a material that is less rigid than the material of the plunger 400A. For example, the sealing member 404A may be formed from a silicone material, in some embodiments. The sealing member 404A includes opposing straight edges, of which edge 416A is shown. The sealing member 404A further includes opposing curved edges, of which curved edge 418A is shown. The shape of the edges 416 maintains a seal in the channel 306A when compressed against the walls thereof. The curved shape of the edges 418 may reduce friction during actuation of the valve. Additionally, the valve plunger 400A includes an opening 420A through which fluids (including gases and liquids) and solid material may pass.

FIG. 7B presents a perspective view of the valve plunger 400B, which includes many of the features described above in connection with the plunger 400A. Accordingly, the plunger 400B includes the O-ring 402B and the sealing member 404B. The plunger 400B further includes a protrusion 410B that is sized and configured for insertion into the recess 115B of the button 114B. The protrusion 410B includes a notch 412B that corresponds to a boss protruding from the surface of the recess 115B to maintain alignment of the button 114B with respect to the valve plunger 400B. The proximal end of the plunger 400B includes a latch member 414B that includes prongs, like the prongs of the latch member 414A. The valve plunger 400B further includes an opening 420B. In some embodiments, the valve plunger 400A includes an additional O-ring disposed between the latch member 414A and the sealing member 404A. Similarly, the valve plunger 400B may include an additional O-ring disposed between the latch member 414B and the sealing member 404B.

Figures 8A, 8B:
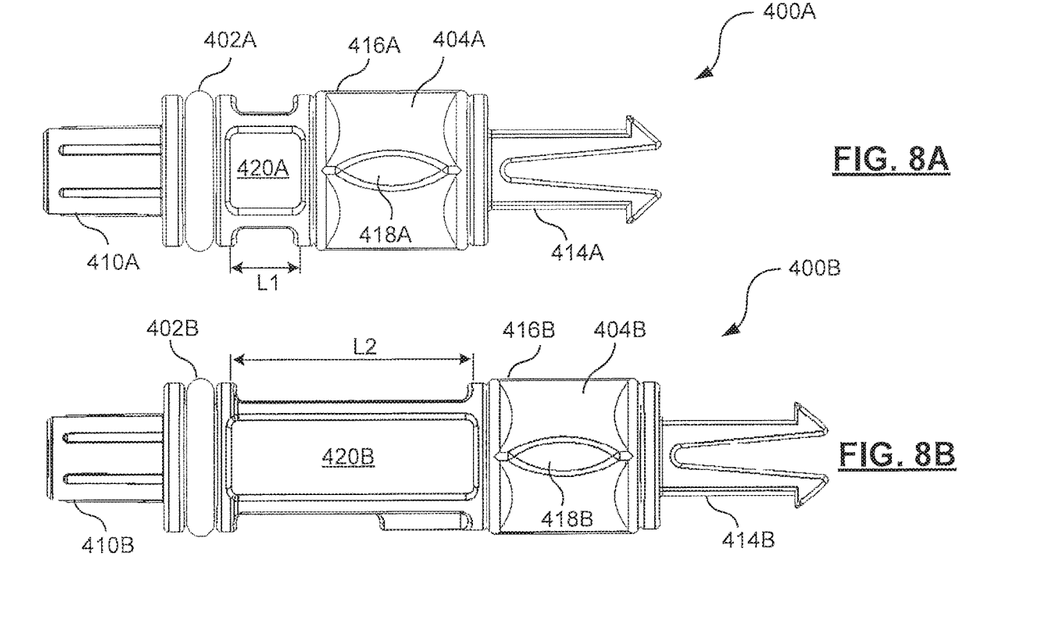
FIGS. 8A and 8B are side views of the valve plungers of FIGS. 7A and 7B, respectively, showing openings in the valve plungers according to some embodiments.

FIGS. 8A and 8B are side views of the valve plungers 400 of FIGS. 7A and 7B, respectively, showing openings therein according to some embodiments. The side views of the plungers 400 shown in FIGS. 8A and 8B provide a perspective looking through the openings 420A and 420B of the plungers 400A and 400B, respectively. While many features of the plungers 400A and 400B are of similar or identical dimensions, the openings 420A and 420B are substantially different. As shown in FIG. 8A, the opening 420A has a length L1. As illustrated in FIG. 8A, the length L1 is about 5 mm. In other embodiments of the valve system 200, the length L1 of the valve plunger 400A may be in a range from about 3 mm to about 10 mm or more. The length L1 is substantially shorter than the length L2, which is the length of the opening 420B in the valve plunger 400B shown in FIG. 8B. As depicted, the length L2 may be about 15 mm. Embodiments of the valve plunger 400B may include an opening 420B having a length L2 that ranges from about 5 mm to about 30 mm. The length L2 of the opening 420B may be greater than the length L1 of the opening 420A, because the opening 420B is configured to convey material along the flow path 300 as well as along the flow path 302, whereas the opening 420A is configured to convey material along the flow path 300 only.

Referring again to FIG. 6B, the valve plungers 400A and 400B are positioned in an extended position, caused by the bias elements 406A and 406B. When both of the valve plungers 400A and 400B are in the extended position as depicted, material is prevented from flowing along either the flow path 300 or the flow path 302. When the valve plunger 400A is compressed against the bias element 406A, whether by manual actuation or a robotic actuation, the opening 420A becomes aligned with the channel 212A, permitting material to pass therethrough. The valve plunger 400B, when in the extended position or in a compressed position, is configured such that the opening 420B is aligned with the channel 212A, because the length L2 is substantially greater in length L1. When the valve plunger 400B is put in a compressed position, whether manually or under robotic actuation, the opening 420B becomes aligned with the channel 212B such that the flow path 302 becomes operative. Accordingly, when the valve plunger 400A is compressed and the valve plunger 400A is extended, the flow path 300 may freely convey material. When the valve plunger 400A is extended and the valve plunger 400B is compressed, the flow path 302 may freely convey material. When both of the plungers are extended, neither the flow path 300 nor the flow path 302 may convey material. When both of the plungers are compressed, both the flow paths 300 and 302 may convey material. The material conveyed may include a gas, liquid, and/or solid material. The flow paths 300 and 302 may convey material in either direction along the flow paths depending upon the pressures provided via the lumens 134, as shown in FIG. 3.

Figure 9A:
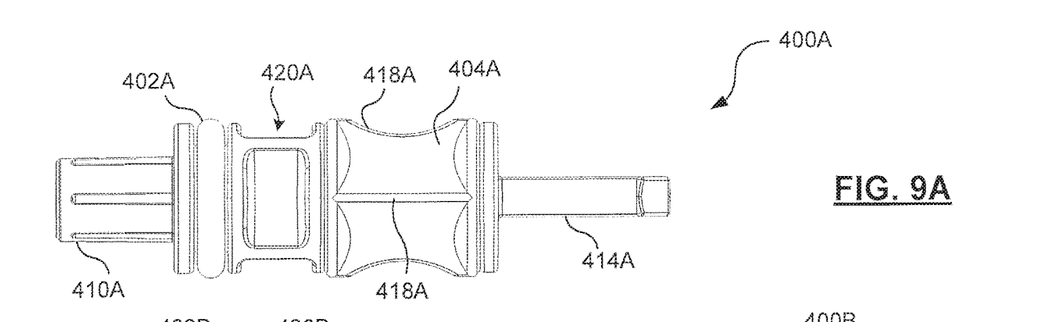
FIGS. 9A and 9B are additional side views of the valve plungers of FIGS. 7A and 7B, respectively, according to some embodiments.
Figure 9B:
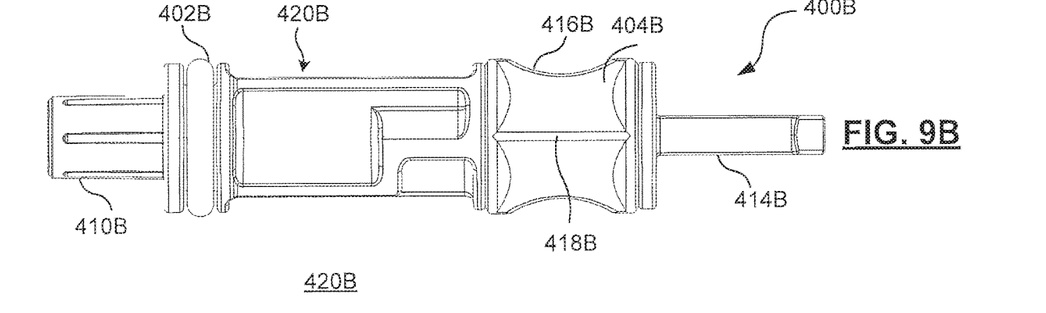

FIGS. 9A and 9B are additional side views of the valve plungers 400A and 400B of FIGS. 7A and 7B, respectively, according to some embodiments. FIGS. 9A and 9B show a different perspective, such that an exterior side wall 422A of the opening 420A is shown in FIG. 9A, while an exterior side wall 422B of the opening 420B is shown in FIG. 9B.

Figure 10:
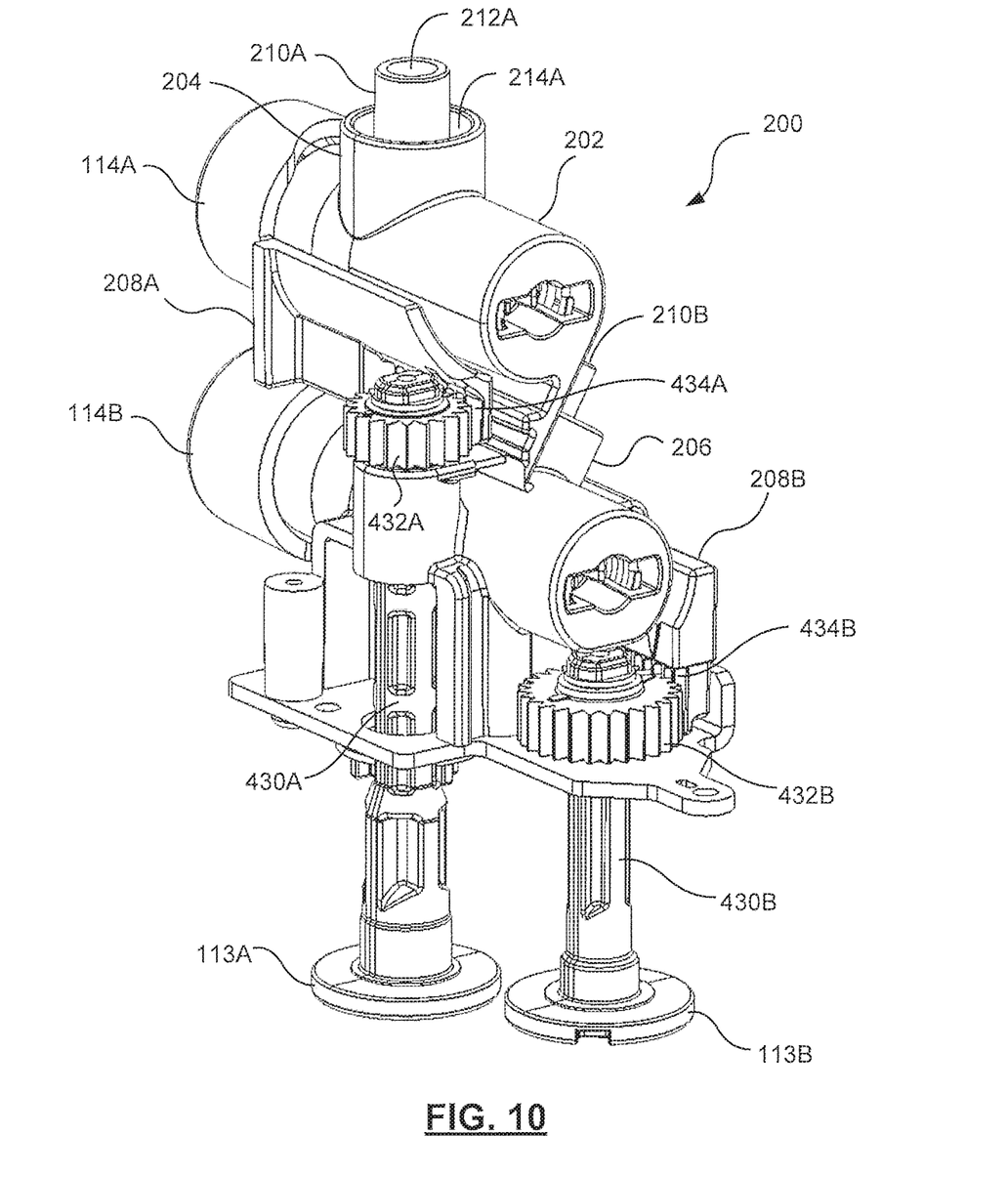
FIG. 10 is a rear perspective view of the valve system, according to some embodiments.

FIG. 10 is a rear perspective view of the valve system 200, according to some embodiments. FIG. 10 provides another view of the interface discs 113A and 113B, collectively referred to as interface discs 113, also shown in FIG. 1. As described herein, the interface discs 113A and 113B enable connection to an instrument interface on a medical robotic system to permit control of the valve system 200 by the medical robotic system. As shown each of the interfaces disc 113 may be coupled at a proximal end to a shaft. In some implementations, the interface discs 113 may be integrally formed with the shafts. The interface disc 113A connects to the proximal end of a shaft 430A. A gear 432A may be connected to the distal end of the shaft 430A. The gear 432A is positioned such that the teeth of the gear 432A interact with a row of teeth 434A formed on a surface of the actuation member 208A. When the robotic system interacts with the interface disc 113A, rotating the disc 113A, the gear 432A rotates and causes the actuation member 208A to translate. The translation of the actuation member 208A may move the valve plunger 400A in a controlled manner to open or close to couple or decouple the distal portion and middle portion of the flow path 300. Similarly, the robotic system may rotate the interface disc 113B, causing the shaft 430B and gear 432B to rotate. The rotation of the gear 432B may cause translation of the actuation member 208B, which has a row of teeth 434B that mesh with the teeth of the gear 432B. In other embodiments of the valve system 200, other mechanisms may be used to couple a medical robotic system to the actuation members 208A and 208B to manipulate the valve plungers 400A and 400B.

Figure 11:
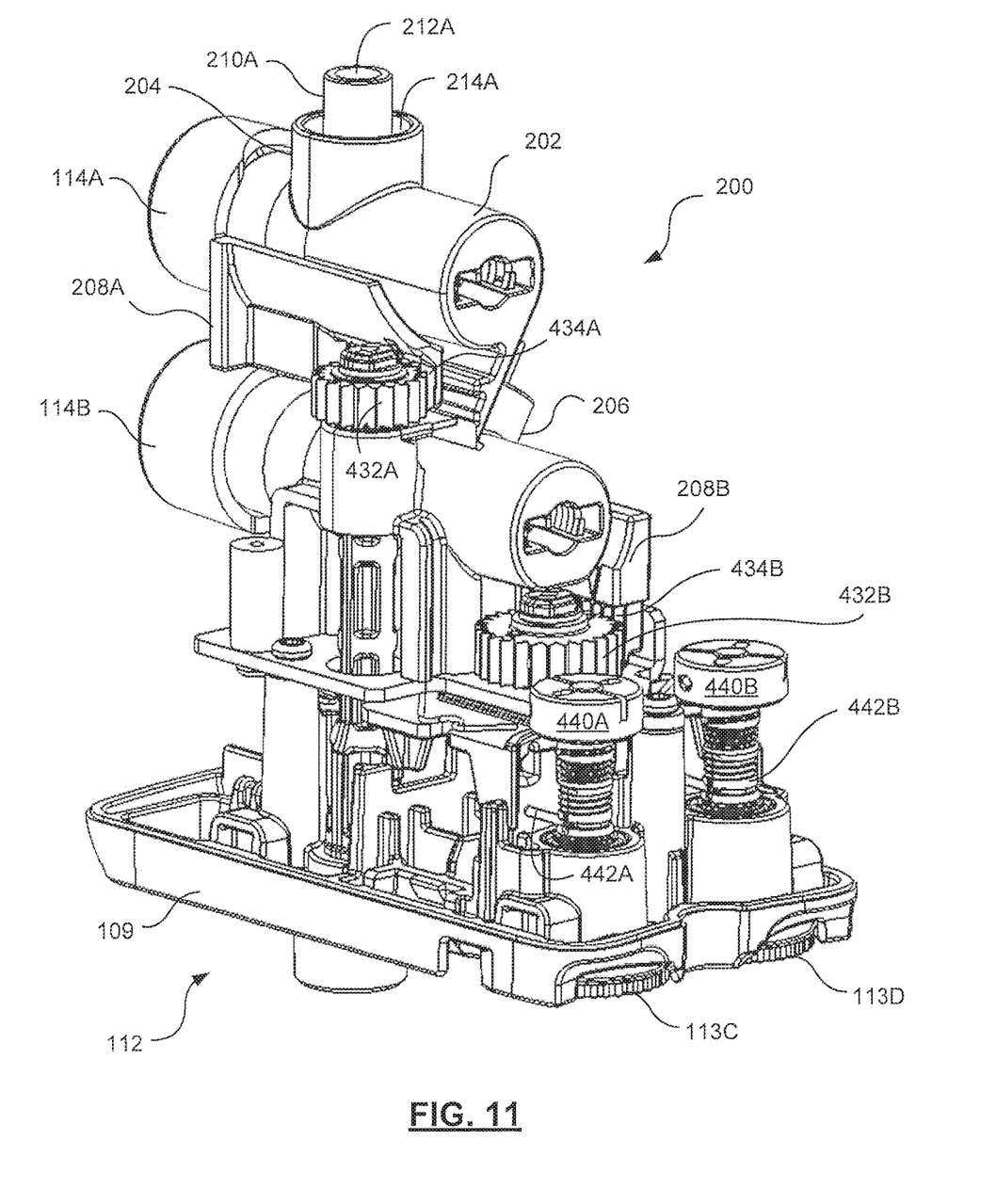
FIG. 11 is a rear perspective view of the valve system, according to some embodiments.

FIG. 11 is another rear perspective view of the valve system 200, according to some embodiments. FIG. 11 provides another view of the valve body 202, and includes features not explicitly depicted in FIG. 10. FIG. 11 shows a review view of the faceplate 109 of the chassis 112 of FIG. 1. In FIG. 11, the view of the shaft 430B is obscured by cable capstans 440A and 440B. The cable capstans 440A and 440B may be connected to interface discs 113C and 113D, respectively. The cable capstans 440A and 440B have respective cables 442A and 442B wound around capstan shafts with one or more windings. The robotic system may the interface with the discs 113C and/or 113D, to manipulate the wrist mechanism 124 and/or the end effector 126 when the medical instrument backend mechanism 110 is connected to the robotic system.

Embodiments of the present disclosure may provide for significant improvements in maintaining the greatest possible suction capacity by providing a straight path for suction and an offset path for irrigation, such as saline or another irrigation material. By lengthening the opening in the valve plunger 400B relative to the opening in the valve plunger 400A, the valve plunger 400B may accommodate both of the straight section path and the offset irrigation path. Such a configuration may provide useful improvements to the performance of suction/irrigation devices.

Aspects of the various embodiments may be combined together. Furthermore, the scope of the present disclosure includes such modifications and adjustments as would be apparent to one of ordinary skill in the art. Accordingly, the scope of the present disclosure is presented with respect to the following claims.

What we claim is:

1. A medical device comprising:
a valve body, in which a first fluid channel and a second fluid channel are defined, wherein the first fluid channel extends through the valve body and comprises a proximal portion, a middle portion, and a distal portion, and wherein the second fluid channel extends into the valve body, wherein a central axis extends through the first fluid channel and the proximal, middle, and distal portions are aligned along the central axis;
a first valve plunger in which a first fluid path is defined, the first valve plunger being movable between a first position, in which the first valve plunger is positioned to obstruct fluid flow between the proximal and middle portions of the first fluid channel, and a second position, in which the first fluid path couples the proximal and middle portions of the first fluid channel; and
a second valve plunger in which a second fluid path is defined, the second valve plunger being movable between a first position, in which the second fluid path is positioned to couple the middle and distal portions of the first fluid channel and to obstruct fluid flow between the second fluid channel and the distal portion of the first fluid channel, and a second position, in which the second fluid path couples the middle and distal portions of the first fluid channel and couples the second fluid channel to the distal portion of the first fluid channel.

2. The medical device of claim 1:
wherein the first valve plunger and the second valve plunger are parallel; and
wherein the first fluid channel is orthogonal to the first valve plunger and to the second valve plunger.

3. The medical device of claim 1:
wherein the first valve plunger and the second valve plunger are parallel;
wherein the first fluid channel is orthogonal to the first valve plunger and to the second valve plunger; and
wherein the second fluid channel is angled away from the first valve plunger.

4. The medical device of claim 1:
wherein the first valve plunger comprises a button comprising a convex top surface; and
wherein the second valve plunger comprises a button comprising a concave top surface.

5. The medical device of claim 4:
wherein the button of the first valve plunger and the button of the second valve plunger are positioned adjacent one another.

6. The medical device of claim 1, wherein fluid flow in the proximal portion of the first fluid channel comprises a fluid suction flow.

7. The medical device of claim 1, wherein fluid flow in the second fluid channel comprises a fluid supply flow.

8. The medical device of claim 1, further comprising an elongate tube in fluid communication with the distal portion of the first fluid channel, the elongate tube being sized and shaped to be slidingly received in a surgical cannula.

9. The medical device of claim 1 wherein the second valve plunger includes an opening through which the second fluid path extends.

10. The medical device of claim 9 wherein the opening provides entrance to a bounded passage through which the second fluid path extends.

* * * * *